United States Patent
Keller et al.

(10) Patent No.: US 7,150,883 B2
(45) Date of Patent: *Dec. 19, 2006

(54) SELF FORMING, THERMODYNAMICALLY STABLE LIPOSOMES AND THEIR APPLICATIONS

(75) Inventors: Brian Charles Keller, Antioch, CA (US); Dan D. Lasic, deceased, late of Fremont, CA (US); by Alenka Lasic, legal representative, Fremont, CA (US)

(73) Assignee: BioZone Laboratories, Inc., Pittsburg, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/178,001

(22) Filed: Jul. 8, 2005

(65) Prior Publication Data

US 2005/0249797 A1 Nov. 10, 2005

Related U.S. Application Data

(63) Continuation of application No. 10/262,284, filed on Sep. 30, 2002, now Pat. No. 6,958,160, which is a continuation of application No. 09/745,292, filed on Dec. 20, 2000, now Pat. No. 6,610,322.

(51) Int. Cl.
*A61K 9/127* (2006.01)

(52) U.S. Cl. ..................... 424/450; 428/402.2

(58) Field of Classification Search ............ 424/450, 424/1.21, 9.321, 9.51, 417
See application file for complete search history.

(56) References Cited

U.S. PATENT DOCUMENTS

| | | | |
|---|---|---|---|
| 5,225,212 A | 7/1993 | Martin et al. | |
| 5,358,714 A * | 10/1994 | Green | 424/400 |
| 5,415,869 A * | 5/1995 | Straubinger et al. | 424/450 |
| 5,720,973 A | 2/1998 | Rosenberg et al. | |
| 5,741,515 A | 4/1998 | Ciceri et al. | |
| 5,807,573 A * | 9/1998 | Ljusberg-Wahren et al. | 424/450 |
| 5,859,228 A | 1/1999 | Janjic et al. | |
| 5,912,272 A | 6/1999 | Hoppe et al. | |
| 6,110,492 A * | 8/2000 | Alving et al. | 424/450 |
| 6,610,322 B1 * | 8/2003 | Keller et al. | 424/450 |
| 6,734,171 B1 * | 5/2004 | Saravolac et al. | 514/44 |
| 6,958,160 B1 * | 10/2005 | Keller et al. | 424/450 |

FOREIGN PATENT DOCUMENTS

| | | |
|---|---|---|
| EP | 0 211 647 | 8/1985 |
| EP | 0 707 847 | 10/1994 |
| JP | 2000247868 | 9/2000 |
| WO | 94/19019 | 2/1993 |

OTHER PUBLICATIONS

International Search Report, BIOZ-0001PCT, International Application PCT/US 01/50118, mailed Nov. 7, 2002.

* cited by examiner

*Primary Examiner*—Gollamudi S. Kishore
(74) *Attorney, Agent, or Firm*—Thelen Reid & Priest LLP; Lee M. Pederson

(57) ABSTRACT

A lipid composition forms liposomes spontaneously upon mixing with an aqueous solution. The lipid composition includes diacylglycerol-PEG compounds. Such lipid compositions are useful for forming liposomes, which in turn are useful for a variety of purposes, including the delivery of therapeutic agents.

5 Claims, 5 Drawing Sheets

PEG-12 Glyceryl Dioleate

PEG-12 Glyceryl Dioleate

SELF FORMING, THERMODYNAMICALLY STABLE LIPOSOMES AND THEIR APPLICATIONS

CROSS-REFERENCE TO RELATED APPLICATION

This application is a continuation of and claims priority based on co-pending U.S. patent application Ser. No. 10/262,284 entitled "Self Forming, Thermodynamically Stable Liposomes and Their Applications", filed on Sep. 30, 2002 now U.S. Pat. No. 6,958,160, in the name of the same inventors and commonly owned herewith; which is a continuation of and in turn claims priority based on U.S. Pat. No. 6,610,322, which issued from U.S. patent application Ser. No. 09/745,292, entitled "Self Forming, Thermodynamically Stable Liposomes and Their Applications", filed on Dec. 20, 2000, in the name,of the same inventors and commonly owned herewith.

FIELD OF THE INVENTION

The present invention relates to liposomes. More particularly, the present invention relates to liposomes which form spontaneously upon mixing of lipids and an aqueous solution, and applications thereof.

BACKGROUND OF THE INVENTION

Liposomes are self-closed colloidal particles in which membranes composed of one or more lipid bilayer(s) encapsulate a fraction of the aqueous solution in which they are suspended. The surfaces of bilayers are hydrophilic while the interior of bilayers, which contain hydrocarbon chains, are hydrophobic. Because of the different microenvironments in their structure, liposomes can encapsulate hydrophilic molecules, bind molecules on the bilayer surfaces or dissolve hydrophobic molecules into the middle of the bilayer. Their ability to incorporate many types of molecules has resulted in applications for drug delivery, diagnostics, cosmetics, cosmeceuticals and nutraceuticals.

Liposomes are manufactured by several different methods. Typically, the process begins when a lipid or combination of lipids are dissolved in an organic solvent. Upon removal of organic solvents and hydration, large multilamellar vesicles (MLVs) are formed. For some applications, small unilamellar vesicles (SUVs) may be desired. SUVs can be produced from MLVs by several techniques including sonication, extrusion through membranes with well-defined pores, French press extrusion and homogenization.

Problems associated with liposomes include colloidal instability, difficulty in scale-up sterilization, and variability between batches in manufacturing. Liposome preparation and manufacturing typically involves removal of organic solvents followed by extrusion or homogenization. These processes may expose liposomal components to extreme conditions such as elevated pressures, elevated temperatures and high shear conditions which can degrade lipids and other molecules incorporated into the liposomes.

Liposome preparations are often characterized by very heterogeneous distributions of sizes and number of bilayers. Conditions optimized on a small scale normally do not scale up well and preparation of large-scale batches is cumbersome and labor intensive.

Another issue associated with liposomes for medical uses is sterilization. Among heat sterilization, ethanol oxide exposure, gamma irradiation and sterile filtration, only the last technique is suitable for liposomes and then only for liposomes smaller than about 100 nanometers (nm). Filtration of liposomes poses many difficulties.

Another problem for liposome applications is colloidal stability. Liposomes in suspension can aggregate and fuse upon storage, heating and addition of various additives. Because of these stability problems, liposomes are often lyophilized. Lyophilization is costly and time consuming. Upon reconstitution, size distributions often increase and encapsulated materials may leak out from the liposomes.

It is therefore desirable to develop new methods and materials which address these problems with current liposome formulations.

BRIEF DESCRIPTION OF THE INVENTION

A liposome suspension forms spontaneously upon adding a lipid composition to an aqueous solution. The lipid composition comprises a single lipid or a mixture of lipids that have appropriate packing parameters, that includes polyethyleneglycol, and that has a melting temperature which allows it to be in liquid form when mixed with the aqueous solution. Such liposome suspensions are useful for a variety of purposes, including the delivery of therapeutic agents.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Figure 1:
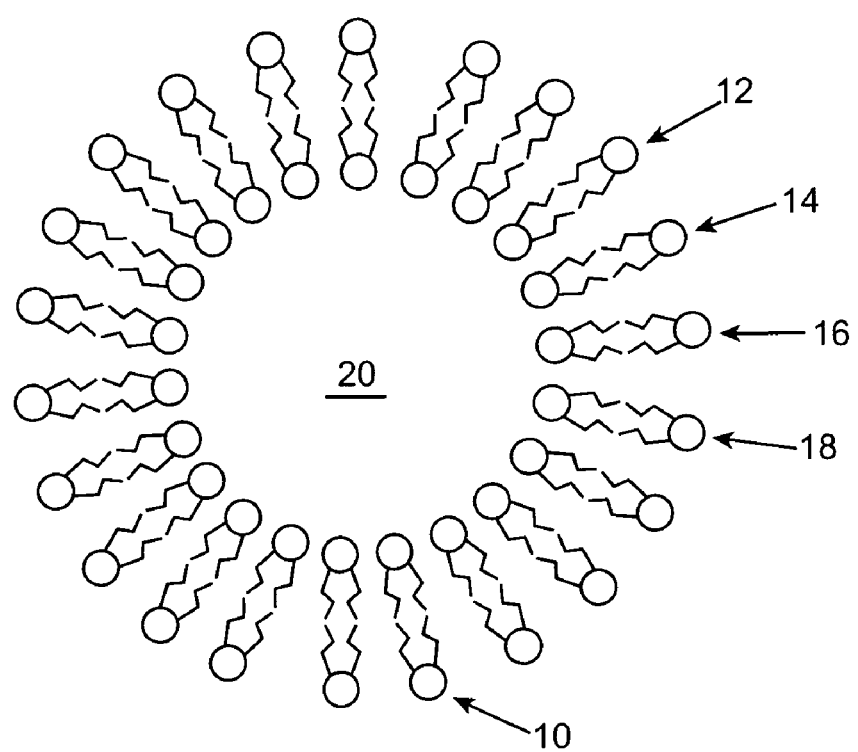
FIG. 1 is a diagram depicting the cross-section of a liposome made of lipid molecules.

Embodiments of the present invention are described herein in the context of a self-forming, thermodynamically stable liposomes and their applications. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Those of ordinary skill in the art will realize that the following description of the present invention is illustrative only and not in any way limiting. Other embodiments of the invention will readily suggest themselves to such skilled persons having the benefit of this disclosure.

Most, if not all, known liposome suspensions are not thermodynamically stable. Instead, the liposomes in known suspensions are kinetically trapped into higher energy states by the energy used in their formation. Energy may be provided as heat, sonication, extrusion, or homogenization. Since every high-energy state tries to lower its free energy, known liposome formulations experience problems with aggregation, fusion, sedimentation and leakage of liposome associated material. A thermodynamically stable liposome formulation which could avoid some of these problems is therefore desirable.

The present invention teaches liposome suspensions which are thermodynamically stable at the temperature of formation. The formulation of such suspensions is achieved by employing a composition of lipids having several fundamental properties. First, the lipid composition must have packing parameters which allow the formation of liposomes. Second, as part of the head group, the lipid should include polyethyleneglycol (PEG) or any polymer of similar properties which sterically stabilizes the liposomes in suspension. Third, the lipid must have a melting temperature which allows it to be in liquid form when mixed with an aqueous solution.

By employing lipid compositions having the desired fundamental properties, little or no energy need be added when mixing the lipid and an aqueous solution to form liposomes. When mixed with water, the lipid molecules disperse and self assemble as the system settles into its natural low free energy state. Depending on the lipids used, the lowest free energy state may include small unilamellar vesicle (SUV) liposomes, multilamellar vesicle (MLV) liposomes, or a combination of SUVs and MLVs.

Lipid compositions suitable for use in the invention may include compositions comprising only a single type of lipid molecule as well as compositions made up of more than one lipid. As will be appreciated by those skilled in the art, both types of compositions may be quantified according to cited fundamental properties.

One required fundamental property is the ability to form liposomes by virtue of having the proper packing parameters. Packing parameters are relative measures of a given lipid composition, and depend on factors such as size relationships between lipid head groups and lipid hydrocarbon chains, charge, and the presence of stabilizers such as cholesterol. (Israelachvili, D D Lasic, Liposomes: From Physics to Applications, Elsevier, pp 51, 1993).)

To form a lipid bilayer, lipid head groups and hydrocarbon chains must organize themselves so that the radius of curvature results in a liposome (see FIG. 1). If the hydrocarbon chains are too small relative to the head group, the radius of curvature will be too large and micelles will be produced (see FIG. 3). If the hydrocarbon chains are too large relative to the head groups, the radius of curvature will be of the opposite sign and liposomes cannot form (see FIG. 4).

FIG. 1 is a diagram depicting the cross-section of a liposome made of lipid molecules. Liposome 10 comprises a lipid bilayer, made of lipid molecules (e.g., 12, 14, 16, 18), enclosing an aqueous space 20.

Figure 2:
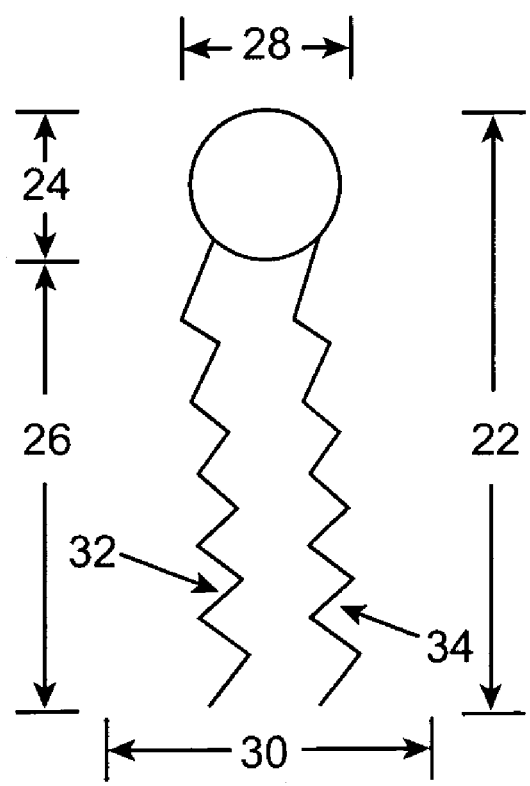
FIG. 2 is a space-filling diagram of a lipid molecule having a polar head group and nonpolar hydrocarbon chains.

FIG. 2 is a space-filling diagram of a lipid molecule having a polar head group and nonpolar hydrocarbon chains. Lipid molecule 22 is comprised of a hydrophilic group 24 and a hydrophobic tail 26. Hydrophobic tail 26 may comprise two hydrocarbon chains 32, 34. While its chemical bonds allow the lipid molecule to be flexible, the head group generally fills an area of diameter 28 while the tail fills an area of diameter 30. Because lipid molecules must be organized in a bilayer to form a liposome, the ratio of the head group diameter to the tail diameter can be neither too large nor too small if liposome formation is to occur.

Figure 3:
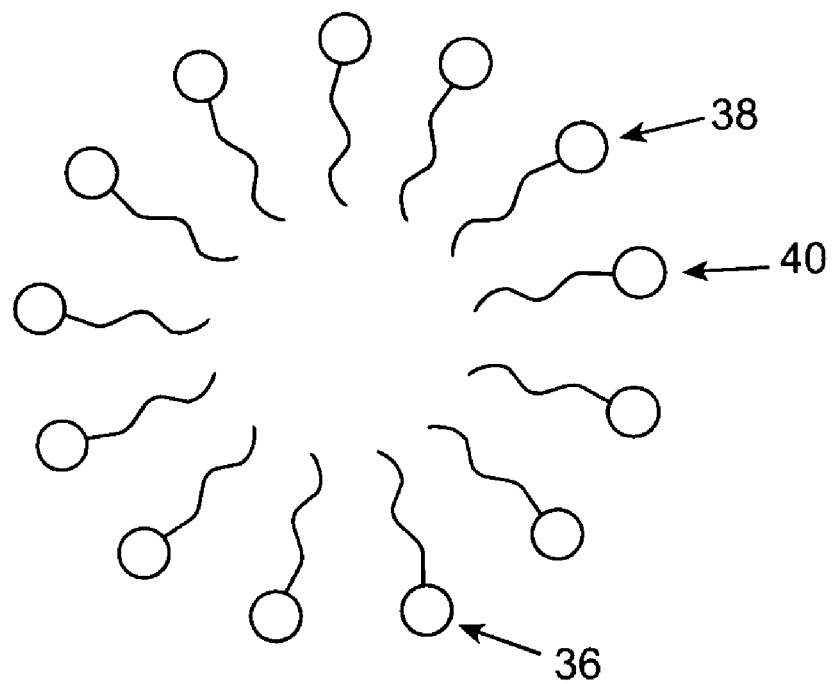
FIG. 3 is a diagram depicting a cross-section of a micelle made of lipid molecules.

FIG. 3 is a diagram depicting a cross-section of a micelle made of lipid molecules. Micelle 36 is composed of lipid molecules (e.g., 38, 40). Because the tail groups of the lipid molecules have small diameters relative to the head groups, the lipid molecules organize with a small radius of curvature, and a bilayer cannot form.

Figure 4:
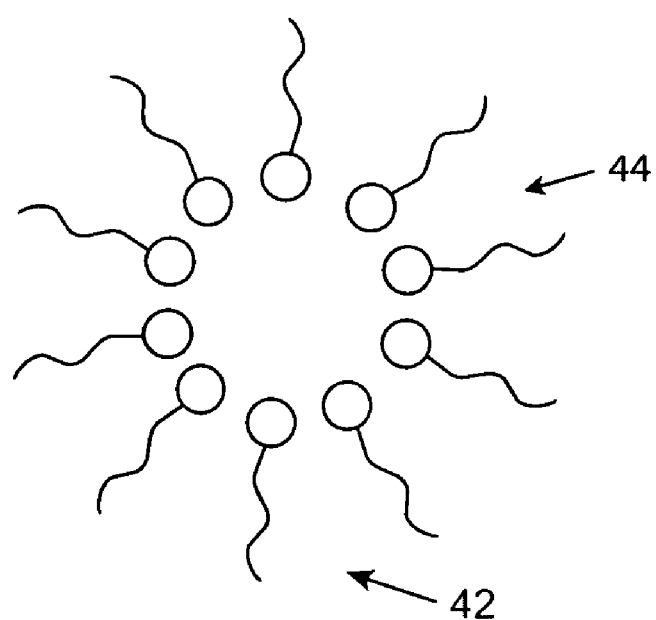
FIG. 4 is a diagram depicting a cross-section of a structure made of lipid molecules with large tails relative to the head groups.

FIG. 4 is a diagram depicting a cross-section of a structure made of lipid molecules with large tails relative to the head groups. In FIG. 4, it can be seen that structure 42 forms when lipids (e.g., 44) having large tails relative to the head groups are mixed in aqueous solution. Again, the size ratio between head groups and tails makes bilayer formation impossible.

While FIGS. 1, 3 and 4 have illustrated the basic principle of packing parameters using a single type of lipid molecule, it will be appreciated that the same principle applies to mixtures of lipids. For example, a lipid which has hydrocarbon chains too small to form liposomes as a single species can be mixed with cholesterol to result in a composition which has the proper packing parameters. As another example, a lipid which by itself has the proper packing parameters may form liposomes incorporating limited amounts of other lipids which, by themselves, do not have proper packing parameters. Both single lipids and mixtures of lipids have packing parameters that may be calculated by known methods. In general, liposome compositions which allow liposome formation have packing parameter measurements of $P_a$ between about 0.84 and 0.88 and $P_v$ between about 0.88 and 0.93.

$P_a$ is the packing parameter with respect to surface and $P_v$ is packing parameter with respect to volume (DD Lasic, Liposomes:From Physics to Applications, Elsevier, pp 51, 1993). The parameters are derived from the equations $HC_a/T_a \equiv P_a$ and $HC_v/T_v \equiv P_v$ where $HC_a$ is the hydrocarbon chain area, $T_a$ is the total area of the molecule, $HC_v$ is the volume of the hydrocarbon chain and $T_v$ is the volume of the whole molecule.

Packing parameters can be calculated for mixtures of lipids, since ideal mixing of lipids results in arithmetic average of their individual characteristics. For instance $HC_a/T_a \equiv P_a$ of a binary mixture, in the case of ideal mixing can be expressed as:

$$<P_a> = X_1 P_1 + X_2 P_2,\ X_1 + X_2 = 1$$

More generally in the case of i lipids composing a given mixture can be represented by:

$$<P_a> = \Sigma_i X_i P_i \text{ and } \Sigma_i X_i = 1$$

where $X_i$ is the mole fraction of the lipid in the mixture and $P_i$ is the packing parameter with respect to surface of that lipid.

Figure 5:
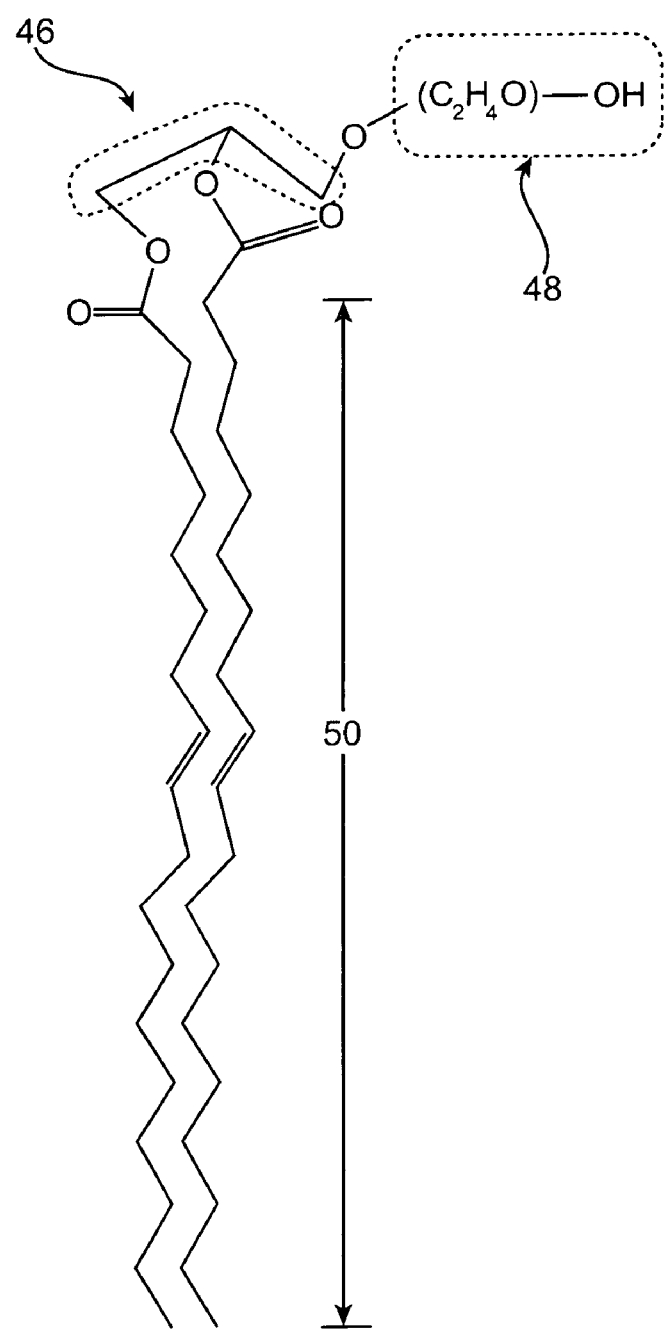
FIG. 5 is a diagram showing the molecular structure of PEG-12 Glyceryl Dioleate or Hetoxamate GDO-12.

FIG. 5 is a diagram showing the molecular structure of PEG-12 Glyceryl Dioleate or Hetoxamate GDO-12 which includes a glycerol backbone 46, a PEG chain 48, and a tail group 50 having two hydrocarbon chains. Together, the backbone 46 and the PEG chain 48 comprise the head group of the molecule. PEG-12 GDO is an preferred lipid molecule for use in the present invention, in part because its head group has the proper size in relation to its tail group.

Two general factors influence the size of the head group in a lipid molecule. One is the actual physical size of the head group. For example, employing a longer PEG chain would make the head group larger. The other is the charge associated with the head group. For example, if the PEG chain was conjugated to the backbone by a phosphodiester bond the phosphate would impart a charge to the head group, effectively increasing its size. In the present invention, non-phospolipids are preferred so that the general means of varying head group size is by varying the length of the PEG chain. However, those skilled in the art will recognize that the effective size of the head group could be varied in other ways, for example by using a different backbone other than glycerol or adding a linker such as phosphate between the glycerol backbone and the PEG chain.

The size of the tail of a lipid is mostly influenced by the length of hydrocarbon chains and degree of saturation in the lipid chain. Single chain lipids will generally not form liposomes, though they may be incorporated into liposomes composed of lipids with two chains. Similarly, lipids with one long chain and one short chain may have relatively small tail sizes. Those skilled in the art will recognize that such lipids may be used to form liposomes in the present invention, especially if sterols such as cholesterol are used to stabilize the bilayer.

A second fundamental property of lipid compositions suitable for use in this invention is that the head group of at least one lipid must include a PEG chain. PEG stabilizes the liposomes by creating a steric barrier at the outer surface of the liposomes. Preferably, the PEG chain have a molecular weight between about 300 Daltons and 5000 Daltons, although those skilled in the art will recognize that differing concentrations of PEG on the liposome surface as well as differing chain lengths may be used to stabilize the liposomes.

A third fundamental lipid property is that the lipid composition must have a melting temperature which allows the composition to be in liquid form when mixed with an aqueous solution. Generally, this means that the lipid composition should have a phase transition temperature of between about 0° C. and 100° C. As with packing parameters, melting temperatures may be determined for mixtures of lipids.

Related to melting point of a lipid is bending elastic modulus. Generally preferred in the present invention are lipids with a bending elastic modulus that allows the lipid to be sufficiently flexible to form liposomes in an aqueous solution without the need for large energy inputs. If the bending elastic modulus is too great, the lipid will be too rigid to spontaneously form liposomes in an aqueous solution. Preferably, the bending elastic modulus is between about 0 kt and 15 kt. More preferably, the bending elastic modulus is between about 1 kt and 10 kt. The bending elastic modulus is largely determined by the backbone. Glycerol provides an ideal backbone for the present invention.

Table 1 shows a number of lipids which have been tested as single lipids for suitability for the present invention. Lipids were tested at 2 weight percent in aqueous solution. Note that GDL means glycerol dilaurate, GDO means glycerol dioleate, GDM means glycerol dimyristate, GDP means glycerol dipalmitate, and GDS means glycerol distearate. For each lipid, the number after "PEG" indicates the numbers of $C_2H_4O$ subunits in the PEG chain. The unsaturated dioleate lipids have similar packing parameters to the saturated dimyristate lipids.

| lipid | melting point (° C.) | $P_a$ | $P_v$ | Spontaneous Liposomes at 20° C. | Spontaneous Liposomes at 37° C. | Spontaneous Liposomes at 60° C. |
| --- | --- | --- | --- | --- | --- | --- |
| PEG-23 GDL | Fluid @ 25 | .829 | .869 | NO | NO | NO |
| PEG-12 GDO | Fluid @ 25 | | | YES | YES | YES |
| PEG-23 GDO | Fluid @ 25 | | | NO | NO | NO |
| PEG-45 GDO | 36.3 | | | NO | NO | NO |
| PEG-12 GDM | Fluid @ 25 | .853 | .889 | YES | YES | YES |
| PEG-23 GDM | Fluid @ 25 | .837 | .875 | NO | NO | NO |
| PEG-45 GDM | 33.2 | .823 | .863 | NO | NO | NO |
| PEG-23 GDP | 31.2 | .843 | .880 | | YES | YES |
| PEG-45 GDP | 41.8 | .828 | .867 | NO | NO | NO |
| PEG-12 GDS | 40.0 | .869 | .901 | NO | NO | YES |
| PEG-23 GDS | 39.8 | .849 | .885 | NO | NO | YES |
| PEG-45 GDS | 40.8 | .830 | .870 | NO | NO | NO |

The table shows that lipids which possess the required properties will spontaneously form liposomes when mixed in an aqueous solution. For example, PEG-12 GDM spontaneously forms liposomes at all temperatures tested since it is a liquid at those temperatures and includes PEG in addition to having packing parameters within the required ranges. Similarly, PEG-12 GDO, which shares nearly identical properties to PEG-12 GDM, spontaneously forms liposomes at all temperatures tested.

PEG-12 GDS shows one example of the requirement that the lipid be liquid at the temperature of liposome formation. While this lipid has the required packing parameters as well as including PEG, it does not spontaneously form liposomes until the temperature of liposome formation is high enough for the lipid to be in liquid form.

The GDM series of lipids illustrates the importance of proper packing parameters. While these lipids all include PEG and are in liquid form at 60 degrees, only PEG-12 GDM has the proper packing parameters to allow spontaneous liposome formation. The GDS lipid series at 60 degrees illustrates the same point.

Those skilled in the art can practice the present invention by using knowledge of the required properties to predict and create lipid compositions which will spontaneously form liposomes. Foe example, certain PEG lipids which form micelles can form liposomes in mixtures with sterols, such as cholesterol, because of cholesterol's effect on packing parameters and melting point. For instance, the mixture of PEG-45 GDS and cholesterol forms liposomes. Similarly, the size of the head group may be changed to affect packing parameters, for example by varying the size of the PEG chain or by varying the concentration of PEG-containing lipids in the lipid composition.

It will be appreciated that, while liposomes form spontaneously at the temperature of formation, cooling of liposomes after formation results in liposomes in trapped kinetic states. To minimize distortions in liposome structure upon such cooling, sterols such as cholesterol may be mixed with the lipid before liposome formation. It has been observed that cholesterol may be dissolved in PEG-12 GDO at up to about 10 percent by weight.

Utility

The present invention is useful in a variety of situations, and provides advantages over the prior art in several different ways. Problems with liposome preparation, reproducibility, colloidal stability, sterilization, and storage may be reduced by employing the invention.

Since the liposomes of the present invention are self-forming, liposome preparation entails merely mixing the lipid with an aqueous solution. In general, liposome formation is scale dependant. It is simple, in the case of the present invention, to scale up from test batches to large batches.

Because the liposomes of the present invention exist in the lowest energy state that the lipid can exist in while in aqueous solution, reproducibility of liposome formation is no problem. A defined lipid, lipid mixture, or lipid/compound mixture will form similar liposomes every time when mixed with the same aqueous solution. It should be noted, however, that above critical concentrations (around 20% weight to volume for most lipids) non-liposomal structures will begin to form in aqueous solution.

Aggregation and fusion may occur with liposomes in thermodynamically trapped states. Because the liposomes of the present invention are in the lowest energy state, they do not aggregate and fuse.

Because the liposomes of the present invention are small, they can be sterile filtered. Also, the lipids may be heat sterilized prior to liposome formation.

As with any liposome dispersion, these liposomes can be lyophilized in the presence of appropriate cryoprotectants. Even in liquid form, the liposomes are colloidally stable because they are a thermodynamically stable system. Also, because of their self-forming nature, the liposomes need not be stored at all. Instead, the lipid may be stored and constituted into liposomes as needed.

Applications of the present liposomes include the delivery of therapeutics and other compounds, use in cosmetics, and use in drug delivery screening.

Since the liposomes include an aqueous space, a hydrophobic region within the bilayer, and sites for covalent attachment (e.g., on the PEG chain or the backbone), many types of compounds may be encapsulated by the liposomes. Such compounds include compounds ranging from hydrophilic to hydrophobic, including many insoluble compounds. These liposomes may substitute for currently available Cremophor® and Solutol®.

For delivery of intravenous drugs, the drug may be provided in a sealed container co-dissolved or co-mixed along with the lipid. The container may also contain inert gas to reduce decomposition of the drug and lipid. Prior to administration an aqueous solution is added to the container, thereby forming liposomes with encapsulated drug. Drugs suitable for such a mode of administration include: proteins, peptides, nucleic acids, antineoplastic agents, anti-inflammatories, anti-infectives, gastrointestinal agents, biological and immunologic agents, dermatologic agents, ophthalmic and otic agents, diagnostic aids, nutrients and nutritional agents, hematological agents, endocrine and metabolic agents, cardiovasculars, renal and genitourinary agents, respiratory agents, central nervous system agents.

In one aspect, the invention includes a method of preparing liposomes. The method comprises providing an aqueous solution; providing a lipid solution, where the solution has a $P_a$ between about 0.84 and 0.88, a $P_v$ between about 0.88 and 0.93, and where at least one lipid in the solution includes a polyethyleneglycol (PEG) chain; and combining the lipid solution and the aqueous solution. The PEG chain preferably has a molecular weight between about 300 Daltons and 5000 Daltons. Kinetic energy, such as shaking or vortexing, may be provided to the lipid solution and the aqueous solution. The lipid solution may comprise a single lipid. The lipid may comprise dioleolyglycerol-PEG-12, either alone or as one of the lipids in a mixture. The method may further comprise providing an active compound; and combining the active compound with the lipid solution and the aqueous solution.

The active compound may be selected from the group comprising proteins, peptides, nucleic acids, antineoplastic agents, anti-inflammatories, anti-infectives, gastrointestinal agents, biological and immunologic agents, dermatologic agents, ophthalmic and otic agents, diagnostic aids, nutrients and nutritional agents, hematological agents, endocrine and metabolic agents, cardiovasculars, renal and genitourinary agents, respiratory agents, central nervous system agents.

In another aspect, the invention includes a liposome suspension. The suspension comprises one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain. The PEG chain preferably has a molecular weight between about 300 Daltons and 5000 Daltons. The suspension may comprise a single lipid. The lipid may comprise dioleolylglycerol-PEG-12. The suspension may further comprise an active compound, which may be selected from the group described above.

In another aspect, the invention includes a composition for combining with an aqueous solution to form a liposome suspension. The composition comprises one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain. The PEG chain preferably has a molecular weight between about 300 Daltons and 5000 Daltons. The composition may comprise a single lipid. The composition may comprise dioleolylglycerol-PEG 12. The composition may further comprise an active compound selected from the group above. The composition may be provided in a sealed container, where the container also contains an inert gas to prevent oxidative degradation.

In another aspect, the invention includes a method of intravenously administering a therapeutic compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing an active compound; providing an aqueous solution; combining the composition, compound and solution to form a liposome suspension; and administering the liposome suspension intravenously. The method may further comprise providing kinetic energy to the liposome suspension. The method may also include providing the composition in a sealed container containing an inert gas. The PEG chain preferably has a molecular weight between about 300 Daltons and 5000 Daltons. The composition may comprise a single lipid. The lipid may comprise dioleolylglycerol-PEG-12. The active compound may be selected from the group above.

In another aspect, the invention includes a method of solubilizing an active compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing the active compound; providing an aqueous solution; and combining the active compound, the lipid and the aqueous solution to form a liposome suspension. The method may further comprise providing kinetic energy to the liposome suspension. The method may include providing the composition in a sealed container containing an inert gas. The PEG chain preferably has a molecular weight between about 300 Daltons and 5000 Daltons. The composition may comprise, a single lipid. The lipid may comprise dioleolylglycerol-PEG-12. The active compound may be selected from the group above.

In another aspect, the invention includes a method of orally administering a therapeutic compound. The method comprises providing a composition including one or more lipids, where the lipids as an aggregate have a $P_a$ between about 0.84 and 0.88, a $P_v$ between about 0.88 and 0.93 and a melting temperature of between about 0 to 100 degrees centigrade; and where at least one lipid includes a polyethyleneglycol (PEG) chain; providing an active compound; providing an aqueous solution; combining the composition, compound and solution to form a liposome suspension; and administering the liposome suspension orally in the form selected from the group comprising a two piece hard gelatin capsule, a soft gelatin capsule, or drops.

The compositions may be administered topically, interorally, vaginally or rectally.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

EXAMPLES

Example 1

Spontaneous Liposomes

Single lipids were tested for their ability to spontaneously form liposomes when mixed with an aqueous solution. PEG-12 GDO was obtained from Global 7 (New Jersey). All other lipids were synthesized for the experiment. For each experiment, water and lipid were separately equilibrated at the appropriate temperature. Two weight percent lipid was added to the aqueous solution, and the solution was analyzed for the presence of liposomes by optical light microscopy, cryo TEM, freeze fracture TEM, or hot stage microscopy. The results of the experiments are shown in Table 1 above.

Example 2

Formation of multilamellar liposomes with cholesterol

Cholesterol, 10 Wt. %, was added to PEG-12 Glyceryl Dioleate and heated to about 60°–70° C., for 15–20 minutes. Water, at room temperature, was added to the heated lipid solution. The mixture was left overnight. Examination of the preparation under a optical microscopic with polarized light at 100 power and 600 power showed mulitlamellar liposomes in the size range of 20 nm to 40 nm. No crystals of cholesterol were observed.

Example 3

Spontaneous Liposomes for intravenously administering therapeutic compounds

| Ingredient | Conc. (% wt) |
| --- | --- |
| Methotrexate | 5 |
| PEG-12 GDO | 10 |
| DI Water | 85 |

Methotrexate (Sigma) was dissolved in PEG-12 Glyceryl Dioleate and gently mixed for about 5 minutes. The resultant mixture was a clear solution. Deionized water was slowly added to the solution and gently mixed. The resultant mixture was a yellow, opaque solution. The preparation was examined under a light microscope with polarized light and showed a suspension of liposomes.

Example 4

Spontaneous liposomes for intravenously administered therapeutic compound and as a drug solubilization vehicle

| Ingredient | Conc. (wt %) |
| --- | --- |
| Cyclosporine A | 0.77 |
| PEG-12 GDO | 4.30 |
| DI Water | 95.23 |

Cyclosporin A (Sigma 49H4066) was mixed with PEG-12 Glyceryl Dioleate by vortexing and sonication for 10 minutes. Water was added and gently mixed. Examination under optical microscope at 600 power showed mulitlamelar liposomes and crystals of cyclosporin A.

Example 5

Spontaneous liposomes with active compounds for dermatology

| Ingredient | Conc. (wt) |
| --- | --- |
| PEG-12 GDO | 18 g |
| Betamethasone diproprionate | 50 mg |
| Cholesterol | 100 mg |
| Uniphen-23 ® | 1.5 mg |
| Water | 80.35 g |

Weighed amounts of PEG-12 Glyceryl Dioleate, Betamethasone diproprionate and cholesterol were combined and heated to 50° C. while mixing. Uniphen-23® and water were combined an heated to 50° C. When mixtures reached temperature they were commingled while stirring gently. Mixture was cooled to room temperature while stirring. Examination by optical microscope at 100× and 600× showed a suspension of multilamellar liposomes.

Example 6

Spontaneous liposomes with active compounds for topical anesthesia

| Ingredient | Conc. |
| --- | --- |
| Tetracaine | 2 g |
| PEG-12 GDO | 20 g |
| Uniphen-23 ® | 1.5 g |
| Water | 76.5 g |

Tetracaine, PEG-12 Glyceryl Dioleate, and Uniphen-23® were mixed together and heated to 40° C. while stirring. Water was heated to 40 degrees C. and added to the tetracaine solution while stirring gently. Mixture was cooled to room temperature. Examination by electron microscope showed LUV's and MLV's.

Example 7

Spontaneous liposomes for intravenous and topical formulations

Tretinoin (all-trans retinoic acid), 6 mg, was dissolved in 500 ul of PEG-12 Glyceryl Dioleate. Dissolution was complete. Distilled water, 4.5 ml, was added to the mixture and gently mixed. This yielded a concentration of 1 mg/ml. Examination by optical microscope showed multilamellar liposomes in the size range of 100 nm to 200 nm. This solution can easily be incorporated into a cream, gel or lotion dosage form.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A composition for use in preparing a liposomal formulation of a therapeutic agent, the composition comprising:
   one or more lipids where the total lipids have a $P_a$ between about 0.84 and 0.88 and a $P_v$ between about 0.88 and 0.93,
   where $P_a$ is the packing parameter with respect to surface and $P_v$ is the packing parameter with respect to volume,
   where one or more of the lipids is a diacylglycerol-PEG having a melting point below about 40 degrees C. and also having acyl chains greater than 14 carbons in length, and the therapeutic agent.

2. The composition of claim 1, where the PEG chain of the diacylglycerol-PEG has a molecular weight between about 300 Daltons and 5000 Daltons.

3. The composition of claim 1, where the diacylglycerol-PEG comprises dioleolylglycerol-PEG-12.

4. The composition of claim 1, where the therapeutic compound is selected from the group consisting of proteins, peptides, nucleic acids, agents for treating neoplasms, agents for treating inflammation, agents for treating infections, agents for treating gasterointestinal diseases, agents for treating immunological diseases, agents for treating skin diseases eye diseases, agents uses in diagnosing disease, nutrients, agents for treating blood diseases, agents for treating metabolic diseases, agents for treating cardiovascular diseases, agents for treating renal diseases, agents for treating genitourinary diseases, agents for treating respiratory diseases, and agents for treating central nervous system diseases.

5. The composition of claim 1, where the composition is provided in a sealed container containing an inert gas.

* * * * *